(12) United States Patent
Crawley et al.

(10) Patent No.: US 10,751,433 B2
(45) Date of Patent: Aug. 25, 2020

(54) SYSTEMS AND METHODS FOR CONTROLLING AN IRRADIATION DEVICE

(71) Applicant: Fenwal, Inc., Lake Zurich, IL (US)

(72) Inventors: Brett T. Crawley, Itasca, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 345 days.

(21) Appl. No.: 15/807,916

(22) Filed: Nov. 9, 2017

(65) Prior Publication Data

US 2018/0147306 A1    May 31, 2018

Related U.S. Application Data

(60) Provisional application No. 62/426,643, filed on Nov. 28, 2016.

(51) Int. Cl.
    *A61L 2/24*     (2006.01)
    *A61L 2/00*     (2006.01)
    *A61M 1/02*     (2006.01)

(52) U.S. Cl.
    CPC ............. *A61L 2/0047* (2013.01); *A61L 2/24* (2013.01); *A61M 1/025* (2013.01); *A61L 2202/14* (2013.01); *A61L 2202/22* (2013.01); *A61M 2205/051* (2013.01); *A61M 2205/3368* (2013.01); *A61M 2205/3379* (2013.01); *A61M 2205/3393* (2013.01)

(58) Field of Classification Search
    CPC ...... A61L 2/0047; A61L 2/24; A61L 2202/14; A61L 2202/22; A61M 1/025; A61M 2205/051; A61M 2205/3368; A61M 2205/3379; A61M 2205/3393
    See application file for complete search history.

(56) References Cited

U.S. PATENT DOCUMENTS

| 5,385,539 A | * | 1/1995 | Maynard | ................ G01N 21/51 |
| | | | | 600/322 |
| 5,951,509 A | | 9/1999 | Morris | |
| | | (Continued) | | |

OTHER PUBLICATIONS

European Patent Office, European Search Report, counterpart EP Appl. No. 17203683, dated Apr. 24, 2018.

*Primary Examiner* — Walter D. Griffin
*Assistant Examiner* — Cameron J Allen
(74) *Attorney, Agent, or Firm* — Cook Alex Ltd.

(57) ABSTRACT

A method and system for treating a biological fluid within a container by subjecting the container to light is provided. The system includes a fluid treatment chamber for receiving the container of biological fluid; an agitation assembly for oscillating the container of biological fluid within the fluid treatment chamber including a variable speed motor; one or more light sources in proximity to the fluid treatment chamber; at least one sensor for sensing a condition of the biological fluid in the container; and a programmable controller. The programmable controller is further configured to operate the variable speed motor to oscillate the container of biological fluid within the fluid treatment chamber at an initial oscillation rate; activate the one or more light sources; receive a signal indicative of one or more sensed conditions of the fluid in the container; and vary the speed of the motor to adjust the oscillation rate of the container of biological fluid within the fluid treatment chamber based on the sensed conditions.

11 Claims, 4 Drawing Sheets

(56) References Cited

U.S. PATENT DOCUMENTS

| | | |
|---|---|---|
| 7,433,030 B2 | 10/2008 | Waldo et al. |
| 8,296,071 B2 | 10/2012 | Edrich et al. |
| 9,320,817 B2 | 4/2016 | Walker et al. |
| 2002/0008210 A1 | 1/2002 | Mausbach et al. |
| 2003/0165398 A1* | 9/2003 | Waldo .................. A61L 2/0011 422/22 |
| 2015/0037305 A1* | 2/2015 | Cordisco ............. B01F 11/0002 424/93.73 |
| 2017/0028121 A1 | 2/2017 | Manzella et al. |
| 2017/0029776 A1 | 2/2017 | Cork et al. |

* cited by examiner

SYSTEMS AND METHODS FOR CONTROLLING AN IRRADIATION DEVICE

FIELD OF THE DISCLOSURE

The present application relates to devices, methods and systems for processing and treating biological fluids, such as blood and blood components. More particularly, this application relates to devices, methods and systems involving irradiation of biological fluids, such as blood and blood components, in a container disposed in a treatment chamber.

DESCRIPTION OF RELATED ART

An irradiation device is particularly useful in the treatment of biological fluids. As used herein, biological fluid refers to any fluid that is found in or that may be introduced into the body including, but not limited to, blood and blood products. As used herein, "blood product" refers to whole blood or a component of whole blood such as red blood cells, white blood cells, platelets, plasma or a combination of one or more of such components that have been separated from whole blood.

For example, an irradiation device may be used in the treatment of a blood product that has been combined with a photochemical agent for activation when subjected to light. Such photochemical agents are used, for example, in the inactivation of viruses, bacteria, and other contaminants (collectively referred to herein as "pathogens"). Photochemical agents are also used in the treatment of mononuclear cells, such as white blood cells. In pathogen inactivation applications, the activated agent inactivates pathogens that may be present in a blood product. In the treatment of mononuclear cells, the activated agent targets the mononuclear cell itself as part of a treatment of a disease or a side effect of a mononuclear cell therapy.

Typically, the biological fluid to be treated is introduced into a fluid treatment chamber within the irradiation device in flexible, plastic, sterilizable, translucent, biologically compatible containers. The containers may be integrally connected to other containers and plastic tubing useful in the processing of the biological fluid both before and after the treatment provided by the irradiation device.

One such irradiation device is described in U.S. Pat. No. 7,433,030. The device includes a fluid carrying drawer with a central cavity to allow for placement of a container-carrying tray. A mechanism for oscillating the fluid carrying drawer is provided so that, during treatment of the biological fluid, the fluid within the fluid carrying drawer is agitated, thus mixing of the biological fluid and ensuring that substantially all of the biological fluid is sufficiently and uniformly exposed to light and/or any photochemical agent.

SUMMARY

There are several aspects of the present subject matter that may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

By way of the present disclosure, a system and method are provided by which the rate of agitation of the fluid carrying drawer, and thus the mixing action of the biological fluid in the treatment container, is controlled based on a sensed condition of the biological fluid in the treatment container. The sensed condition may be one or more of the amount of light energy to which the treatment container is exposed, the hematocrit of the fluid in the treatment container, the volume or weight of the fluid in the treatment container, the viscosity of the fluid in the treatment container, the temperature of the fluid in the treatment container, the amount of air in the treatment container, and the density of the fluid in the treatment container.

Thus, the mixing rate can be adjusted based on the sensed conditions to achieve an optimal mixing of the biological fluid within the treatment container, avoiding both under-mixing (which could result in the uneven treatment of the cellular contents of the treatment container) and over-mixing (which could result in undue stress on the cells, air bubble formation, and potentially hemolysis).

More specifically, in a first aspect, an apparatus for treating a biological fluid within a container by subjecting the container to light is provided comprising a fluid treatment chamber for receiving the container of biological fluid; an agitation assembly for oscillating the container of biological fluid within the fluid treatment chamber including a variable speed motor; one or more light sources in proximity to the fluid treatment chamber; at least one sensor for sending a condition of the fluid in the treatment container.

By way of example, the sensor may be one or more of a light sensor for sensing the energy of the light emitted by the one or more light sources, a hematocrit sensor for sensing the hematocrit of the fluid in the treatment container, a volume or weight detector or scale for measuring the volume or weight of the fluid in the treatment container, a viscosity detector for measuring the viscosity of the fluid in the treatment container, a temperature sensor for measuring the temperature of the fluid in the treatment container, an air detector for determining the amount of air in the treatment container, and a density detector for determining the density of the fluid in the treatment container.

A programmable controller is provided that is configured to operate the variable speed motor to oscillate the agitation assembly that holds the container of biological fluid within the fluid treatment chamber at an initial oscillation rate; activate the one or more light sources; receive a signal from one or more of the sensors described above, and then to vary the speed of the motor to adjust the oscillation rate of the container of biological fluid within the fluid treatment chamber based on the sensed condition(s). The programmable controller may also limit the oscillation rate to less than a predetermined maximum.

In one example the sensor may be a light sensor that measures the energy of the light emitted by the one or more light sources upon or after activation to obtain an initial light energy value $J_O$. After an interval of time $t_1$, the energy of the light emitted by the one or more light sources is measured to obtain a light energy value $J_{r1}$. Then, the difference $\Delta J$ between $J_O$ and $J_{r1}$ is determined; and the speed of the motor is varied to adjust the oscillation rate of the container of biological fluid within the fluid treatment chamber based on $\Delta J$.

In a second aspect, a method for treating a biological fluid within a container by subjecting the container to light is provided that uses an apparatus including a fluid treatment chamber for receiving the container of biological fluid, an agitation assembly for oscillating the container of biological fluid within the fluid treatment chamber including a variable-speed motor, one or more light sources in proximity to the container of biological fluid when placed within the fluid treatment chamber, and at least one sensor for sensing a condition of the biological fluid in the treatment container. The sensor may be one or more of a light sensor for sensing the energy of the light emitted by the one or more light sources, a hematocrit sensor for sensing the hematocrit of the fluid in the treatment container, a volume or weight detector or scale for measuring the volume or weight of the fluid in the treatment container, a viscosity detector for measuring the viscosity of the fluid in the treatment container, a temperature sensor for measuring the temperature of the fluid in the treatment container, an air detector for measuring the amount of air in the treatment container, and a density detector for determining the density of the fluid in the treatment container.

The method comprises: placing the container of biological fluid in the fluid treatment chamber; selecting an initial oscillation rate for oscillating the agitation assembly; oscillating the agitation assembly at the initial oscillation rate; activating the one or more light sources; sensing one or more of the of the conditions of the biological fluid in the container; and varying the speed of the motor to adjust the oscillation rate of the agitation assembly based on sensing one or more of the conditions set forth above.

By way of example, the sensed condition may be the energy of the light emitted by the one or more light sources upon or after activation to obtain an initial light energy value $J_O$. Then, after an interval of time $t_1$, sensing the energy of the light emitted by the one or more light sources to obtain a light energy value $J_{t1}$; determining the difference $\Delta J$ between $J_O$ and $J_{t1}$; and varying the speed of the motor to adjust the oscillation rate of the agitation assembly based on $\Delta J$.

In another aspect, the system and method provide for determining a total light energy to which the container is to be subjected; determining a cumulative light energy to which the container has been subjected; comparing the cumulative light energy to the pre-determined total light energy; and deactivating the light sources and the agitation assembly once the cumulative light energy equals or exceeds the pre-determined total light energy.

In another aspect, the system and method provide for increasing the oscillation rate if $\Delta J$ is positive and decreasing the oscillation rate if $\Delta J$ is negative; ii) increasing the oscillation rate if the hematocrit is higher than a predetermined value and decreasing the oscillation rate if the hematocrit is less than a predetermined value; iii) increasing the oscillation rate if the volume or weight is higher than a predetermined value and decreasing the oscillation rate if the volume or weight is less than a predetermined value; iv) increasing the oscillation rate if the viscosity is higher than a predetermined value and decreasing the oscillation rate if the viscosity is less than a predetermined value; v) increasing the oscillation rate if the temperature is higher than a predetermined value and decreasing the oscillation rate if the temperature is less than a predetermined value; vi) decreasing the oscillation rate if the volume of air is higher than a predetermined value and increasing the oscillation rate it the volume of air is less than a predetermined value; and/or vii) increasing the oscillation rate if the density is higher than a predetermined value and decreasing the oscillation rate if the density is less than a predetermined value.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
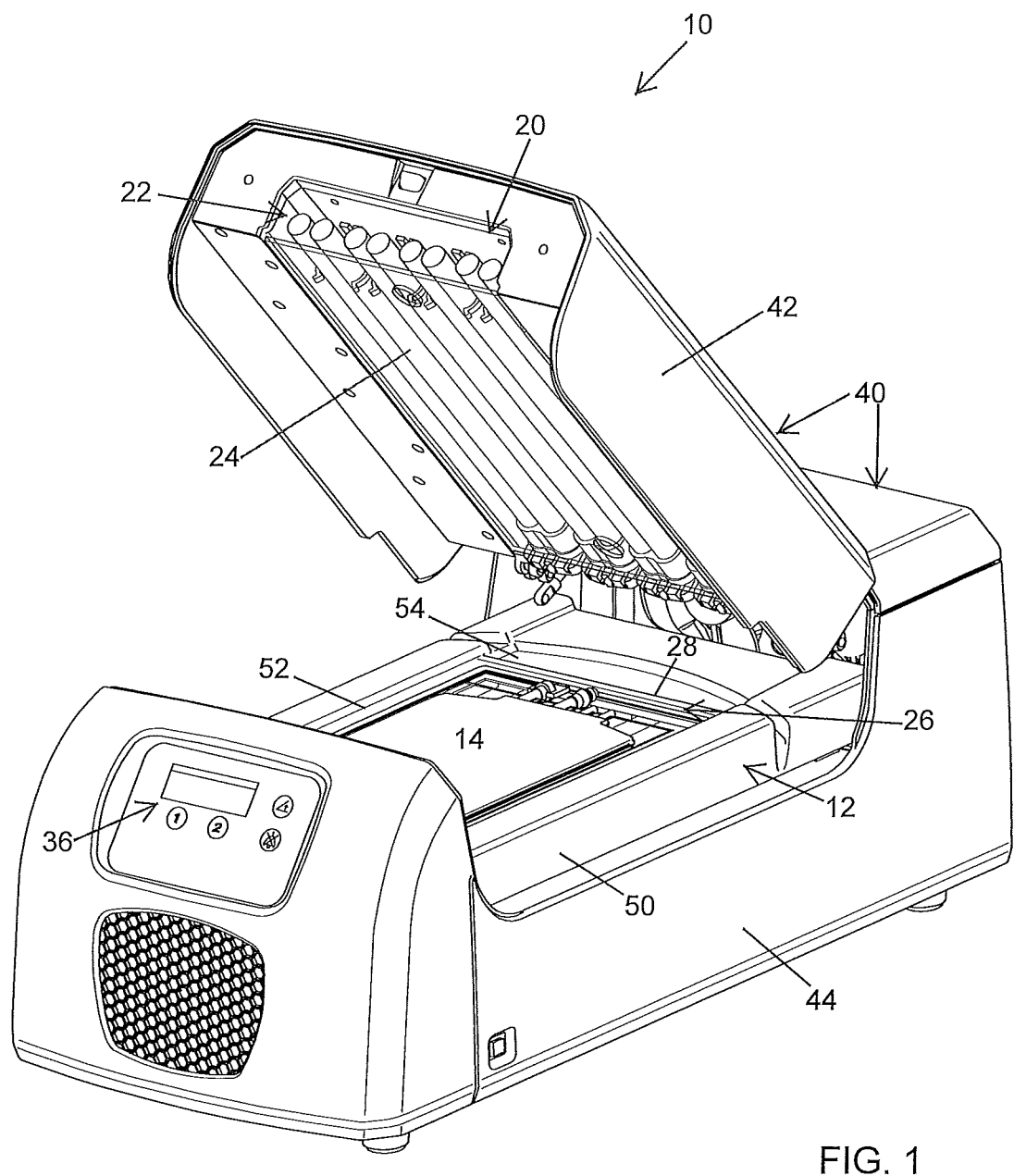
FIG. 1 is a perspective view of an embodiment of a device used to irradiate a collection of cells in a biological fluid container disposed on a tray.

As illustrated in FIG. 1, an irradiation device 10 includes a fluid treatment chamber 12 configured to receive a biological fluid container 14, fluid treatment chamber 12 having opposing first and second sides. Container 14 is suitable for irradiation by light of a selected wavelength. By "suitable for irradiation", it is meant that the walls of the container are sufficiently translucent to light of the selected wavelength. In treatments using UVA light, for example, container walls made of ethylene vinyl acetate (EVA) are suitable.

Figure 2:
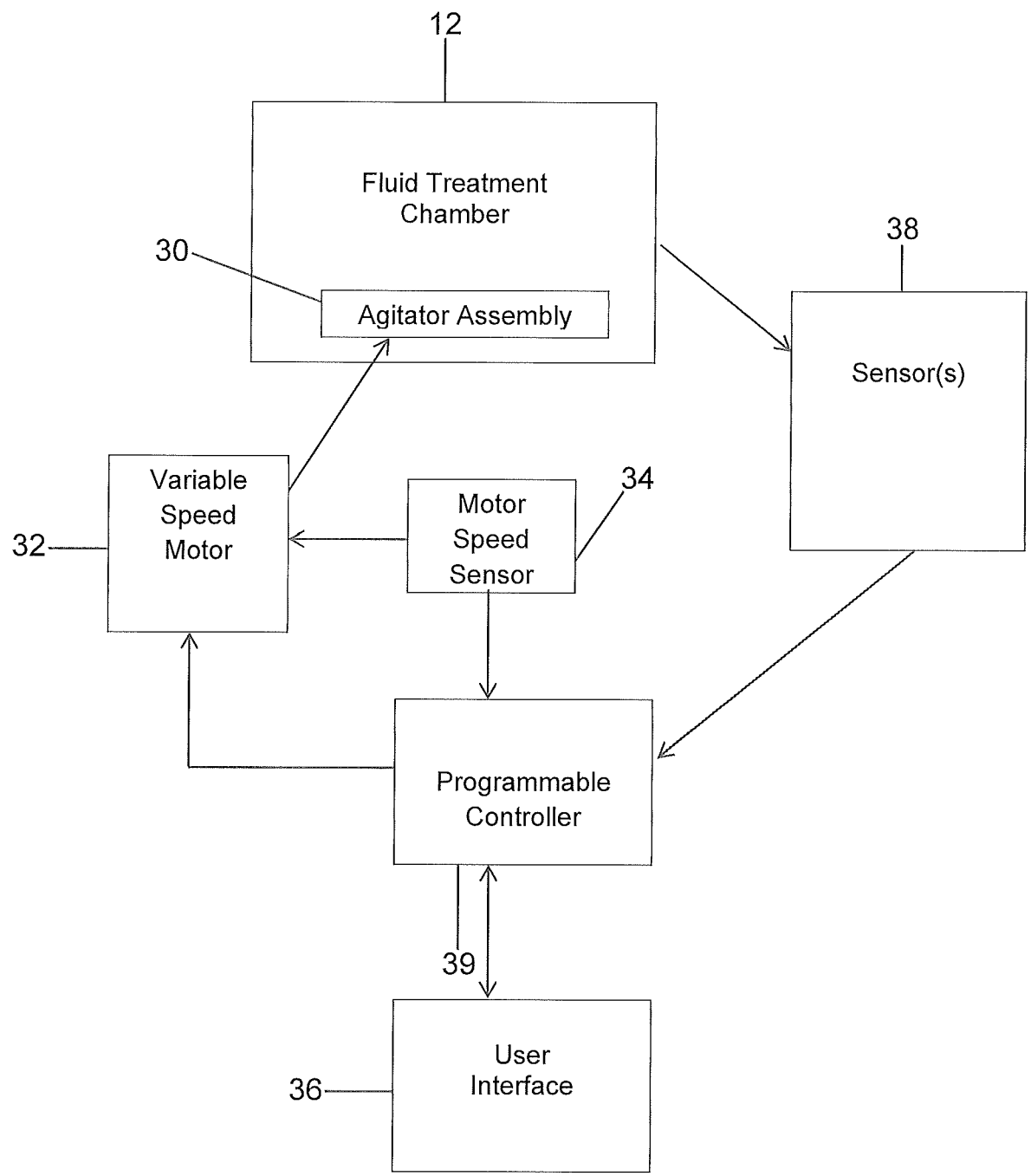
FIG. 2 is a block diagram of an embodiment of the electronic components of the irradiation device of FIG. 1.

As illustrated in FIGS. 1 and 2, device 10 also includes at least one light source 20 disposed adjacent at least one of the first and second sides of the fluid treatment chamber 12. Light source 20 may include, for example, a first array 22 with a plurality of light sources 24 disposed on the first side of the fluid treatment chamber 12 and a second array 26 with a plurality of light sources 28 disposed on the second side 18 of fluid treatment chamber 12. According to an embodiment of the present disclosure, light sources 26, 28 are similar in structure and operation, and provide electromagnetic radiation in the ultraviolet portion of the spectrum (e.g., UVA). An alternative device is described in U.S. Pat. No. 7,433,030, the contents of which are incorporated by reference herein in its entirety.

As illustrated schematically in FIG. 2, device 10 includes an agitator assembly 30 coupled to fluid treatment chamber 12 to move at least a part of fluid treatment chamber 12 with an oscillatory motion. The agitator assembly 30 may include a motor 32 in combination with a linkage (such as a rotating cam), the linkage coupling the motor to fluid treatment chamber 12. An embodiment of an agitator assembly is described in the afore-mentioned U.S. Pat. No. 7,433,030, which has been incorporated herein. By way of example, the agitator assembly 30 may cause fluid treatment chamber 12, or at least biological fluid container 14 disposed in fluid treatment chamber 12, to move in an oscillatory fashion over a distance of 2.54 cm (1 inch). Optionally, a motor speed sensor 34 may be associated with the motor 32 for more accurately controlling the speed of the motor.

One or more sensors 38 (e.g., one or more of a UV sensor, a hematocrit sensor, a volume or weight detector or scale, a viscosity detector, a temperature sensor, an air detector, and a density detector) are disposed within the fluid treatment chamber for measuring a condition of the biological fluid in the fluid container 14. Preferably, the sensors 38 are mounted within the fluid treatment chamber in proximity to the fluid. According to different embodiments, a single sensor 38 may be provided, or a plurality of sensors 38 may be provided to measure the various sensed conditions.

In one embodiment the sensor 38 is a one or more light energy sensors (e.g., UV sensor ML8511-00FCZ05B from Rohm Semiconductor) that is disposed within the fluid treatment chamber for measuring the amount of light energy to which the fluid container 14 is subjected. Preferably, the light energy sensors are mounted within the fluid treatment chamber in proximity to the fluid container so as to more accurately measure the light energy reaching the fluid container 14. According to different embodiments, a single sensor 8 may be provided, or a plurality of sensors 38 may be provided.

Irradiation device 10 also includes a user interface 36 (FIGS. 1 and 2) and a controller 39 (FIG. 2). For the purposes of controlling the rate of oscillation of the fluid treatment chamber 12, controller 39 is coupled to the user interface 36, the sensors 38, and the variable speed motor 32 and motor speed sensor 34. Controller 39 may be coupled directly, or through other intermediary equipment, such as signal processing equipment in the case of the sensors 34 and 38. The motor 32, sensors 34, 38 and interface 36 may have their own power sources, or they may share a power source with, or be powered through, the controller 39.

Device 10 may also include a housing 40 in which fluid treatment chamber 12 is defined, and in which light source 20, agitator 30, motor 32, and sensors 34, 38 are disposed. Controller 39 may also be disposed in housing 40, while the user interface 36 may be disposed on or outside the housing 40 so as to be readily accessible to the operator. While FIG. 1 illustrates an embodiment of housing 40 including a lid 42 that may be moved pivotally relative to a base 44 to open housing 40 and permit access to fluid treatment chamber 12, it will be recognized that housing 40 may instead include a sliding drawer that permits access to fluid treatment chamber 12. Details as to other features that may be incorporated in the irradiation device 10 are described and shown in U.S. Ser. No. 14/810,058, filed Jul. 27, 2015, published Feb. 2, 2017, as US 2017/0029776, the contents of which is incorporated by reference herein in its entirety.

While controller 39 may take the form of one or more electrical components or circuits, controller 39 comprises a processor and an associated memory according to one embodiment. According to such an embodiment, the processor may be programmed to carry out any of the actions that controller 39 is described as being configured to perform below. The instructions by which the processor is programmed may be stored on the memory associated with the processor, which memory may include one or more tangible non-transitory computer readable memories, having computer executable instructions stored thereon, which when executed by the processor, may cause the one or more processors to carry out one or more actions.

Figure 3:
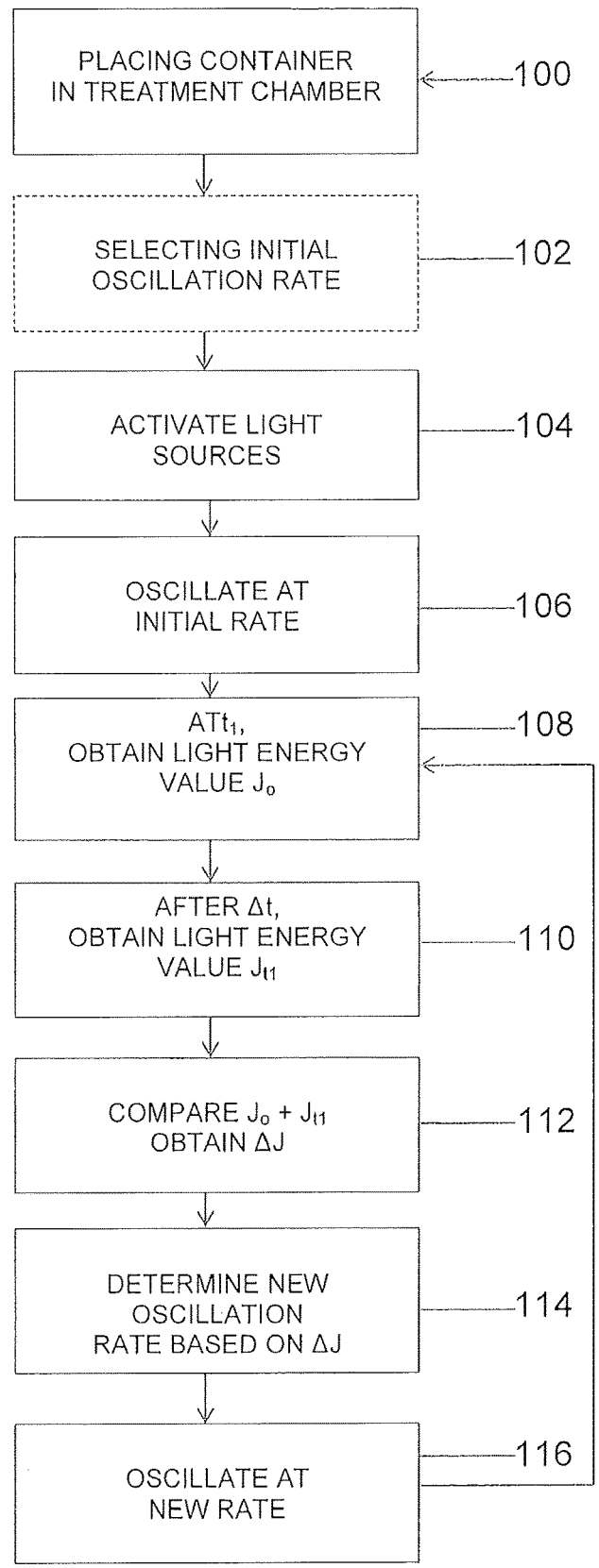
FIG. 3 is a flowchart of a first method in accordance with the present disclosure.

As an example, the controller 38 may be programmed to carry out the following embodiment of a method of operating device 10, as explained with reference to FIGS. 1-3. The method may begin with a determination whether the irradiation cycle should be initiated. A fluid container 14 containing a biological fluid may be placed by an operator in the fluid treatment chamber 12 and the lid 42 closed (step 100). For example, controller 39 may be coupled to a sensor disposed on housing, the sensor generating a signal when a biological fluid container 14 has been disposed in treatment chamber 12, and in particular in tray 50. Alternatively, the controller 39 may be coupled to an input device, such as a keypad, that the user operates after biological fluid container 14 has been disposed in treatment chamber 12. In either event, controller 39 continues to monitor for a signal representative of the fact that the cycle should be initiated until such time as the signal is received.

A total amount of light energy to which the container is to be subjected during the irradiation cycle and/or an initial oscillation rate may be either preprogrammed into the controller or input by the operator through the user interface 36 (step 102). The irradiation cycle may then be initiated, with the light sources 20 being activated (step 104), thereby illuminating biological fluid container 14 in fluid treatment chamber 12. The fluid container 14 is oscillated by activating the agitator at the initial rate (which for some applications may be 0.0 cps (cycles per second))(step 106), thereby agitating biological fluid container 14 (if the initial rate is greater than 0.0 cps) while biological fluid container 14 is illuminated. While FIG. 3 indicates that activation of the light sources (step 104) is initiated before oscillation of the treatment chamber (step 106), this need not be the case: oscillation of the fluid treatment container may precede illumination, or the two may be initiated as approximately the same time (i.e., "simultaneously").

In a first example, the sensors 38 are light sensors. Then, at time, $t_1$, the method continues with controller 39 checking sensors 38 to determine an initial value for the light energy, $J_0$, emitted by the light sources 20 (step 108). $t_1$ may coincide with the initiation of the irradiation cycle, or may be at some time interval thereafter. After a period of time, $\Delta t$, the controller 39 checks the sensors again to determine the current value for the light energy, $J_{t1}$, emitted by the light sources 20 (step 110). The controller 39 then compares the initial light energy value, $J_0$, and the light energy value at time $t_1$, $J_{t1}$, to obtain the difference, $\Delta J$ (step 112). If the absolute value of $\Delta J$ is greater than 0.0 (or some other predetermined amount), the controller 39 will then determine the new oscillation rate (step 114), and adjust the rate of oscillation of the agitator 30 by increasing or decreasing the speed of the motor 32 to oscillate the fluid container at the new rate (step 116).

By way of example, the irradiation cycle may be commenced with an initial oscillation rate (e.g., 0.00 cps) and then after an interval of time (at $t_2$) automatically oscillated a second rate, without regard to the instantaneous light energy value. Then, after a further period of time (at $t_1$), the instantaneous light energy value is determined and compared to the initial light energy value to obtain the difference, and a new oscillation rate determined based thereon. Such a protocol could result in reduced treatment time, by agitating the container at a faster rate near the end of the irradiation cycle to prevent over exposure and to move previously untreated cells closer to the surface of the container to increase their exposure to light energy. Other oscillation protocols may be used that are either pre-programed into the controller, or are input by the operator at the time of use.

For example, if $J_{t1}$ is greater than $J_0$, (i.e., $\Delta J$ is greater than 0.0), then the controller will operate to increase the rate of oscillation. If $J_{t1}$ is less than $J_0$, (i.e., $\Delta J$ is less than 0.0), then the controller will operate to decrease the rate of oscillation. The controller may utilize signals from the motor speed sensor 34 to insure that the motor speed has been adjusted appropriately obtain the new oscillation rate. Under certain circumstances, a maximum rate of oscillation to which the container may be subjected can be pre-programmed into the controller or input into the controller by the operator. Further, it may be desirable that the absolute value of $\Delta J$ be greater than a pre-determined, or an empirically-determined amount greater than 0.0, where an amount of less than the pre-determined amount could be attributable to system noise, before the oscillation rate is varied.

The steps of obtaining a signal indicative of a sensed condition and comparing it to the pre-determined value as described above (i.e., steps 108-116) are repeated at a time interval Δt throughout the irradiation cycle, and the oscillation rate is adjusted accordingly, until such time as the total amount of light energy to be delivered to the container, as either determined by the controller or input by the operator, has been achieved. Preferably, the controller determines a cumulative total of the light energy received by the container during the irradiation cycle, and then automatically deactivates the light sources once the total equals the desired amount.

In a second example, in addition to the sensor(s) 38 being a light sensor, the sensors 38 could be one or more of a sensor for sensing the hematocrit of the biological fluid, the weight of the biological fluid, the volume of the biological fluid, the density of the biological fluid, and the temperature of the biological fluid, and the volume of air in the container. In such circumstances the programmable controller is pre-programmed with a pre-determined standard or base-line value for each of the different sensed conditions, with the predetermined values being determined empirically.

For example, the base-line values are those that by experimentation are shown to provide for the optimal mixing of the biological fluid within the container. The base-line values for the hematocrit may be approximately 2%, the temperature approximately 22° C., the volume of biological fluid approximately 300 ml, and the volume of air in the container approximately 3 ml, or less. From experiments conducted under these conditions, the base-line values for each of the other sensed conditions can be established.

Figure 4:
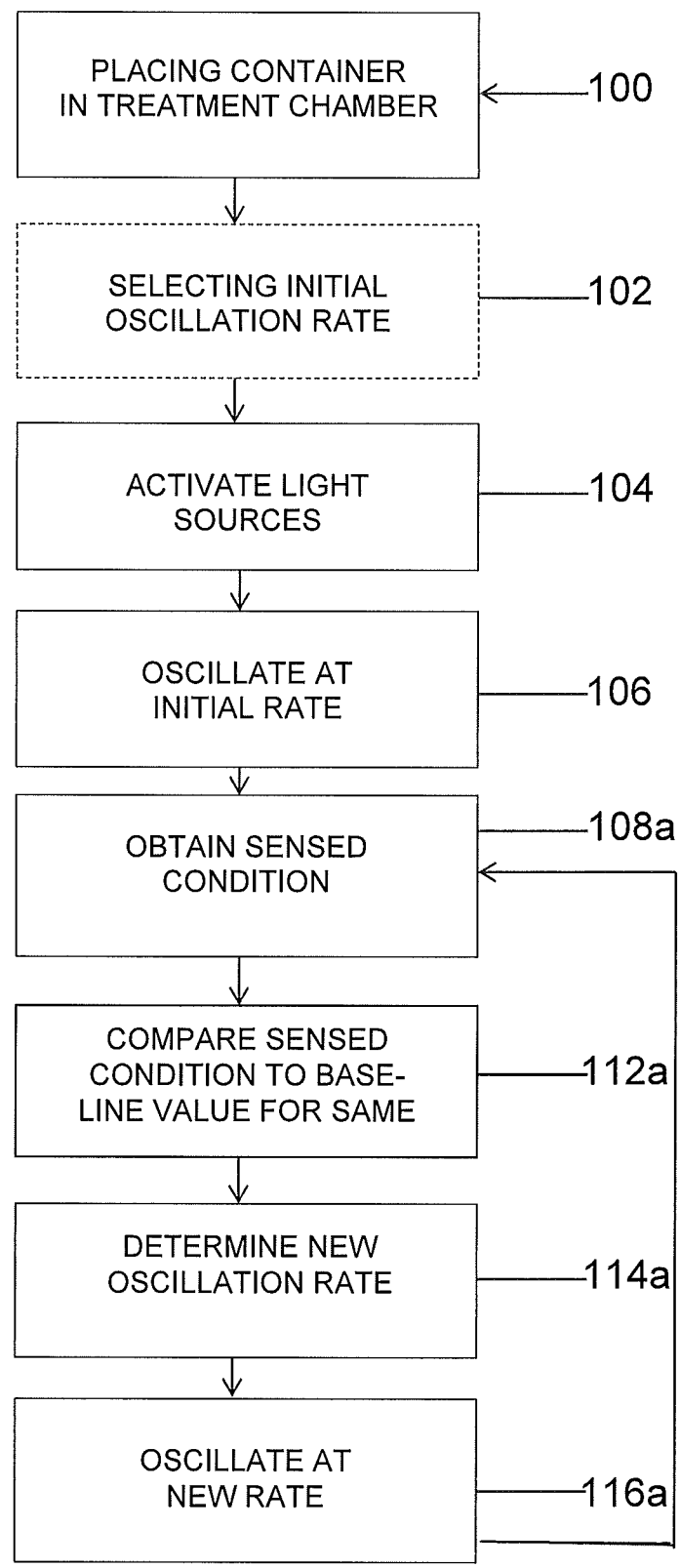
FIG. 4 is a flowchart of a second method in accordance with the present disclosure.

With reference to FIG. 4, steps 100, 102, 104 and 106 are substantially the same as described above with respect to FIG. 3. Then controller will receive a signal from one or more sensors indicative of the various sensed conditions (step 108a), compare the signal to the pre-determined base-line value for the particular sensed condition (step 112a), determine the new oscillation rate based on the sensed condition (step 114a) and the oscillation rate accordingly (Step 116a).

If the sensed condition is the energy of the light emitted by the light sources, the oscillation rate is varied as described above. If the sensed condition is the hematocrit of the biological fluid, the oscillation rate is increased if the hematocrit is higher than the predetermined value and decreased if the hematocrit is less than the predetermined value. If the sensed condition is the volume or weight of the biological fluid, the oscillation rate is increased if the volume or weight is higher than the predetermined value and decreased if the volume or weight is less than the predetermined value. If the sensed condition is the viscosity of the biological fluid, the oscillation rate is increased if the viscosity is higher than the predetermined value and decreased if the viscosity is less than the predetermined value. If the sensed condition is the temperature of the biological fluid, the oscillation rate is increased if the temperature is higher than the predetermined value and decreased if the temperature is less than the predetermined value. If the sensed condition is the volume of air in the container, the oscillation rate is decreases if the volume of air is higher than the predetermined value and increased if the volume of air is less than the predetermined value. If the sensed condition is the density of the biological fluid, the oscillation rate is increased if the density is higher than the predetermined value and decreased if the density is less than the predetermined value.

The effect of the sensed conditions on the rate of oscillation can be additive. For example in the light energy is greater than -0-, the oscillation rate will be increased by a set amount and if, simultaneously, the viscosity is lower than the predetermined value, the oscillation rate will be decreased by a set amount. The two changes for the oscillation rate will be added together to result in the net change in oscillation rate.

It should be noted that while the temperature and viscosity can vary over the course of a procedure, and thus are time sensitive, the volume of the biological fluid, the hematocrit, and the volume of air in the treatment container should remain essentially constant and thus will be measured at only one point in time over the course of the procedure, resulting in an initial, one-time adjustment to the oscillation rate based thereon.

As noted above, the irradiation cycle may be commenced with an initial oscillation rate (e.g., 0.00 cps) and then after an interval of time automatically oscillated a second rate, without regard to the instantaneous light energy value. Then, after a further period of time, the instantaneous light energy value is determined and compared to the initial light energy value to obtain the difference, and a new oscillation rate determined based thereon. Further, the steps of obtaining a signal indicative of a sensed condition and comparing it to the pre-determined value as described above (i.e., steps 108a-116a) are repeated periodically throughout the irradiation cycle, and the oscillation rate is adjusted accordingly, until such time as the total amount of light energy to be delivered to the container, as either determined by the controller or input by the operator, has been achieved.

In addition, the controller can be configured to accelerate and decelerate the fluid treatment chamber at a controlled rate to segregate within the fluid container the different cellular components of the biological fluid being treated based on the mass or density of the cellular components.

To the extent that the mass or density of the cellular components is affected by degree to which they have been irradiated, the cellular components that have received a lower dosage of light energy can be migrated to a region of the fluid container where a greater dosage can be received, e.g., adjacent the walls of the container to receive a higher dose, while the cellular components that have received a higher dosage are displaced to the interior of the container to receive a lesser dose. Thus, a more even dosage of all the cellular components may be obtained.

Alternatively, the cellular components that are segregated based their weight or density can be migrated to a portion of the container that facilitates their selective extraction (e.g., adjacent an extraction port that is integral with the container).

Further, if the controller senses an unevenness of the intensity of the light being emitted the oscillation rate of the fluid treatment container can be accelerated/decelerated to migrate the cellular components to a location within the fluid treatment container that is receiving the higher intensity light.

Without limiting any of the foregoing, the disclosed device, method and system may include one or more of the aspects set forth below.

In a first aspect, a method for treating a biological fluid within a container by subjecting the container to light is provided that uses an apparatus including a fluid treatment chamber for receiving the container of biological fluid, an agitation assembly for oscillating the container of biological fluid within the fluid treatment chamber including a variable-speed motor, one or more light sources in proximity to the container of biological fluid when placed within the fluid treatment chamber, and one or more sensors for sensing one or more conditions of the biological fluid within the container, such as the energy of the light emitted by the one or more light sources.

The method comprises: placing the container of biological fluid in the fluid treatment chamber; selecting an initial oscillation rate for oscillating the container of biological fluid within the fluid treatment chamber; oscillating the container of biological fluid at the initial oscillation rate; activating the one or more light sources; sensing the one or more conditions of the biological fluid, and varying the oscillation rate accordingly. In one example, if the conditioned sensed is the energy of the light emitted by the one or more light sources upon or after activation to obtain an initial light energy value $J_O$; after an interval of time $t_1$, sensing the energy of the light emitted by the one or more light sources to obtain a light energy value $J_{t1}$; determining the difference $\Delta J$ between $J_O$ and $J_{t1}$; and varying the speed of the motor to adjust the oscillation rate of the container of biological fluid based on $\Delta J$.

In a related aspect, a system for treating a biological fluid within a container by subjecting the container to light is provided comprising a fluid treatment chamber for receiving the container of biological fluid; an agitation assembly for oscillating the container of biological fluid within the fluid treatment chamber including a variable speed motor; one or more light sources in proximity to the fluid treatment chamber; one or more sensors for sensing one or more conditions of the biological fluid in the container, and a programmable controller. For example, the sensor may be a light sensor for sensing the energy of the light emitted by the one or more light sources.

The programmable controller is further configured to operate the variable speed motor to oscillate the container of biological fluid within the fluid treatment chamber at an initial oscillation rate; activate the one or more light sources; measure the one or more conditions of the biological fluid, and varying the oscillation rate accordingly. In one example, if the conditioned sensed is the energy of the light emitted by the one or more light sources upon or after activation to obtain an initial light energy value $J_O$; after an interval of time $t_1$, measure the energy of the light emitted by the one or more light sources to obtain a light energy value $J_{t1}$; determine the difference $\Delta J$ between $J_O$ and $J_{t1}$; and vary the speed of the motor to adjust the oscillation rate of the container of biological fluid within the fluid treatment chamber based on $\Delta J$.

In another aspect, the system and method provide for determining a total light energy to which the container is to be subjected; determining a cumulative light energy to which the container has been subjected; comparing the cumulative light energy to the pre-determined total light energy; and deactivating the light sources and the agitation assembly once the cumulative light energy equals or exceeds the pre-determined total light energy.

In a further aspect, the system and method provide for determining on a continuous basis the cumulative amount of light energy to which the container is subjected.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is set forth in the following claims.

The invention claimed is:

1. A system for treating a biological fluid within a container, the biological fluid having a hematocrit, volume, weight, viscosity, density, and temperature and the container holding a volume of air, by subjecting the container to light, the system comprising:
    a fluid treatment chamber for receiving the container of biological fluid;
    an agitation assembly for oscillating the container of biological fluid within the fluid treatment chamber including a variable speed motor;
    one or more light sources for emitting light energy in proximity to the fluid treatment chamber;
    one or more sensors for sensing the condition of the energy of the light emitted by the one or more light sources; and
    a programmable controller configured to:
        operate the variable speed motor to oscillate the agitation assembly at an initial oscillation rate;
        activate the one or more light sources;
        receive a signal from the one or more sensors indicative of the energy of light emitted by the one or more light sources; and
        vary the speed of the motor to adjust the oscillation rate of the agitation assembly based on the signal.

2. The system of claim 1 wherein the programmable controller is further configured to i) receive a signal indicative of the energy of the light emitted by the one or more light sources upon or after activation to obtain an initial light energy value $J_O$; ii) after an interval of time $t_1$, measure the energy of the light emitted by the one or more light sources to obtain a light energy value $J_{t1}$; iii) determine the difference $\Delta J$ between $J_O$ and $J_{t1}$; iv) vary the speed of the motor to adjust the oscillation rate of the agitation assembly based on $\Delta J$; and v) increase the oscillation rate if $\Delta J$ is positive and decrease the oscillation rate if $\Delta J$ is negative.

3. The system of claim 2 wherein the programmable controller is further configured to increase or decrease the oscillation rate only if the absolute value of $\Delta J$ is greater than a pre-determined amount.

4. The system of claim 1 wherein the at least one sensor is located within the fluid treatment chamber adjacent the fluid container.

5. The system of claim 2 wherein the programmable controller is further configured to oscillate the container of biological fluid within the fluid treatment chamber at a pre-selected second oscillation rate starting at a time $t_2$, where $t_2$ is less than $t_1$.

6. The system of claim 1 wherein the programmable controller is further configured to limit the rate of oscillation of the container of biological fluid within the fluid treatment chamber to less than a predetermined maximum.

7. The system of claim 1 further comprising a motor speed sensor and the programmable controller is further configured to receive a signal from the motor speed sensor and to adjust the speed of the motor based thereon.

8. The system of claim 1 wherein the programmable controller is further configured to determine a total light energy to which the container is to be subjected;
    determine a cumulative light energy to which the container has been subjected;
    compare the cumulative light energy to the pre-determined total light energy; and
    deactivate the light sources and the agitation assembly once the cumulative light energy equals or exceeds the pre-determined total light energy.

9. The system of claim 8 wherein the programmable controller is further configured to determine the cumulative light energy on a continuous basis.

10. The system of claim 1 further comprising one or more additional sensors for sensing the condition of one or more of the hematocrit of the biological fluid, the weight of the biological fluid, the volume of the biological fluid, the density of the biological fluid, and the temperature of the biological fluid, and the volume of air in the container; the programmable controller is further configured to receive a signal from one or more of the additional sensors indicative of the sensed condition and to vary the speed of the motor to adjust the oscillation rate of the agitation assembly based on the sensed condition.

11. The system of claim 10 wherein the programmable controller is pre-programmed with a pre-determined value for each sensed condition, and is further configured to i) increase the oscillation rate if the hematocrit is higher than the predetermined value and decrease the oscillation rate if the hematocrit is less than the predetermined value; ii) increase the oscillation rate if the volume or weight is higher than the predetermined value and decrease the oscillation rate if the volume or weight is less than the predetermined value; iii) increase the oscillation rate if the viscosity is higher than the predetermined value and decrease the oscillation rate if the viscosity is less than the predetermined value; iv) increase the oscillation rate if the temperature is higher than the predetermined value and decrease the oscillation rate if the temperature is less than the predetermined value; v) decrease the oscillation rate if the volume of air is higher than the predetermined value and increase the oscillation rate it the volume of air is less than the predetermined value; and vi) increase the oscillation rate if the density is higher than the predetermined value and decrease the oscillation rate if the density is less than the predetermined value.

* * * * *